United States Patent [19]

Guire

[11] 3,959,078

[45] May 25, 1976

[54] ENZYME IMMOBILIZATION WITH A THERMOCHEMICAL-PHOTOCHEMICAL BIFUNCTIONAL AGENT

[75] Inventor: Patrick E. Guire, Kansas City, Mo.

[73] Assignee: Midwest Research Institute, Kansas City, Mo.

[22] Filed: May 18, 1973

[21] Appl. No.: 361,545

[52] U.S. Cl.................................. 195/63; 195/68; 195/DIG. 11
[51] Int. Cl.².......................................... C07G 7/02
[58] Field of Search................. 195/63, 68, DIG. 11; 260/112; 424/94; 96/91 R

[56] References Cited
UNITED STATES PATENTS

| 3,479,183 | 11/1969 | Habib et al. ................. 96/91 R X |
| 3,519,538 | 7/1970 | Messing et al. ..................... 195/63 |
| 3,639,558 | 2/1972 | Csizmas et al. ................. 195/63 X |
| 3,817,837 | 6/1974 | Rubenstein et al. ............. 195/63 X |
| 3,843,447 | 10/1974 | Burkoth............................ 195/63 X |

OTHER PUBLICATIONS

Mitz et al., Synthesis of Biologically Active Cellulose Derivatives of Enzymes, Nature, vol. 189, 1961, (pp. 576–577).

*Primary Examiner*—David M. Naff
*Attorney, Agent, or Firm*—Neuman, Williams, Anderson & Olson

[57] ABSTRACT

Enzymes are immobilized by thermochemically attaching to a solid support material a bifunctional agent initially possessing thermochemical-photochemical functional substituents followed by photochemically activating the bifunctional agent and covalently bonding an enzyme thereto. Preferred bifunctional agents are arylazides which allow activation by visible light.

22 Claims, No Drawings

ENZYME IMMOBILIZATION WITH A THERMOCHEMICAL-PHOTOCHEMICAL BIFUNCTIONAL AGENT

The invention described herein was made in the course of or under a grant from the National Science Foundation, an agency of the United States Government.

This invention relates to systems capable of stabilizing and immobilizing enzymes and to resulting stabilized and immobilized enzyme systems.

Enzymes are highly efficient catalysts capable of accelerating various chemical reactions at rates many times higher than the rate at which a particular reaction occurs in the absence of enzymes. Enzymes accomplish these desiderata under mild physiological or life supporting conditions such as at room temperature, atmospheric pressure, mild acidity or alkalinity and so forth, thus avoiding waste of energy and operating hazards frequently associated with the use of other types of catalysts. Moreover, enzymes are highly specific for catalyzing particular chemical reactions, thus reducing pollution due to unwanted by-products. Also, the chemical reactions occurring in living systems may be carried out on a small or large scale in vitro with great efficiency using enzymes as catalysts. However, enzymes are generally fragile, that is, they may be biodegradable and become inactivated by exposure to extremes of temperature, acidity, alkalinity and so forth.

It is one object of this invention to provide matrices or supports to which enzymes can be bound in a stabilized and immobilized condition.

It is a further object of this invention to provide enzyme systems containing an enzyme bound to a matrix in an immobilized and stabilized condition permitting use and recovery of the enzyme systems as desired.

The above and other objects are accomplished according to this invention by treating a solid support material with an activating agent having a dual functionality, that is, an activating agent which is capable of chemically reacting with a solid support material to become associated therewith and which is also capable of entering into association with an enzyme so as to bind the enzyme with the support material.

In one preferred embodiment of the invention, a solid support material is treated with an activating agent containing a thermochemical functional group and a photochemical functional group. The activating agents are reacted thermochemically with a solid support to form an "activated solid matrix" which is then subjected to photochemical reaction with an enzyme to covalently bind the enzyme thereto. The resulting enzyme system on which the enzyme is bound in a stabilized and immobilized condition can be used in any convenient manner to utilize the enzyme activity. For example, the stabilized solid enzyme system can be used in various flow and batch processes with the bound enzyme performing a desired function and after such use the enzyme system can be readily recovered. Covalent coupling or binding of the enzyme to the "activated solid matrix" provides a stable association with the activity of the immobilized enzyme being maintained during periods of storage and usage. The solid form of the stabilized enzyme system affords numerous advantages in use and recovery thereof. Thus, the solid stabilized enzyme system can be conveniently employed in a reaction column to utilize the enzyme activity on fluids being passed through the column. Likewise, the solid enzyme system can be recovered from liquid reaction media by decantation, filtration and the like.

In accordance with one particularly preferred embodiment of this invention, a solid support material is treated with a thermochemical-photochemical bifunctional agent such as, for example, 1-fluoro-2-nitro-4-azidobenzene (4-fluoro-3-nitrophenyl azide), 1-fluoro-2,4-dinitro-5-azidobenzene (5-fluoro-2,4-dinitrophenyl azide) and other derivatives of arylazides containing substituents which allow activation of the azide by visible light and substituents which react thermochemically with support material. Thus, the fluorine may be replaced with alkylamino, alkylcarboxyl, alkylthiol, alkylmethylimidate, alkylisocyanate, alkylisothiocyanate, alkylaldehyde, alkylhalide and other such groups which react with functional groups of support materials. While the azide on a nitrophenyl ring provides advantages in degree of dark stability and susceptibility to activation by visible electromagnetic radiation, other functional groups which generate nitrenes and/or carbenes can be used as the photochemical group for the thermochemical-photochemical bifunctional reagent. Some examples of such useful photochemical groups are alkyl azides, acyl azides, $\alpha$-keto diazo compounds ($\alpha$-diazo ketones, esters, etc.), diazirines and diazoalkanes. Such photochemical reactive groups can be placed on the same molecule with chosen thermochemical reactive groups. The resulting bifunctional activating agents react thermochemically in the dark with solid support material containing a functionally available reactive group; the reaction occurring between the thermochemical group of the activating agent and the reactive group of the solid support material. In the case of the use 4-fluoro-3-nitrophenyl azide with support material containing alkylamine groups, this reaction can be illustrated as follows:

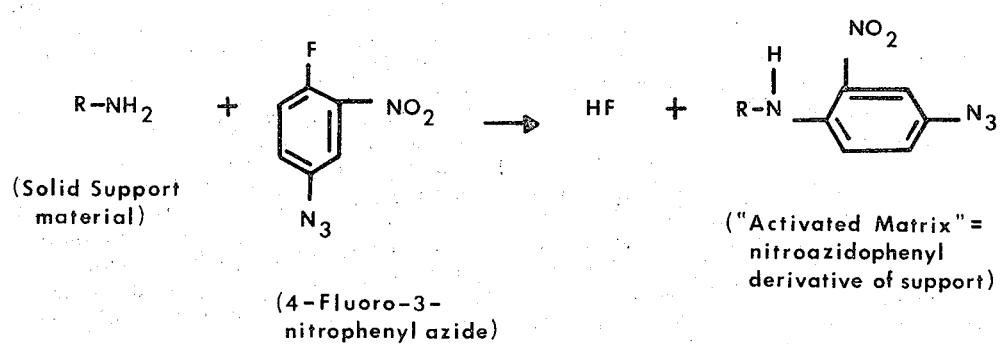

An alternate method of preparing support materials activated with nitroazidophenyl groups is the preparation of dinitrophenyl derivatives of the support materials, the hydrosulfide reduction of these materials, their diazotization by nitrous acid, and substitution by azide ions. These reactions can be illustrated as follows:

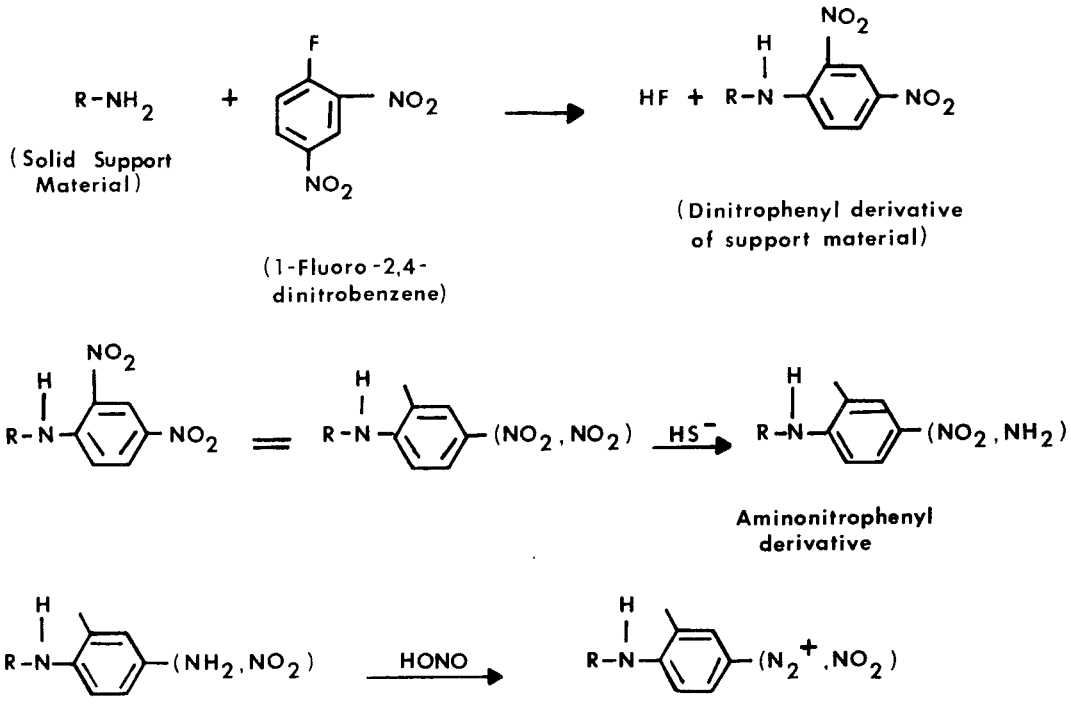

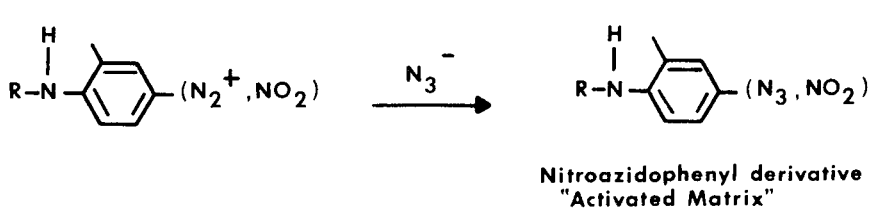

Nitroazidophenyl derivative = "Activated Matrix"

This method produces activated support materials from less expensive starting materials by simple reaction procedures. If one begins with support materials containing alkylamine groups, the excess or unsubstituted groups are converted by the procedure to uncharged alcohol groups.

Since the azide moiety of the activating agents is capable of undergoing photochemical reaction, the reaction with the solid support material is carried out in the dark or in the absence of visible light of such intensity and duration as to affect substantially the photochemically active functionality, that is, for example, subdued daylight for necessary observations, only, with darkness at other times.

Other conditions such as temperature, pressure, pH and the like are not critical insofar as the above reaction is concerned. Generally, however, it is preferred to conduct the reaction at a temperature of from about 25° to 40°C., atmospheric pressure, and at a pH in the range of 7 to 10. The time of reaction will depend upon the temperature, pH and reactivity of the functional groups and in general the reaction can be completed in periods of say 2 to 24 hours. By effecting the above reaction with minimum exposure to visible light, the photochemically functional azide moiety is substantially unaffected and is available for subsequent covalent binding with an enzyme.

The solid support material utilized in the present invention for preparing the "activated matrix" can be any suitable solid material having a substituent capable of chemically reacting with the thermochemically reactive substituent of the activating agent. Examples of suitable solid support materials are the ion exchange glass beads, celluloses, dextrans, agaroses, polyacrylamides, polymethacrylates, silicone rubber elastomers, partially hydrolyzed polyamides and polyesters, collagen and the like.

The nitroazidophenyl derivative of the solid support material, herein referred to as the "activated matrix" is stable in the absence of light and can be reacted with an enzyme to form a solid stable and immobilized enzyme system. To prepare such a solid stabilized enzyme system, the "activated matrix" is contacted with an enzyme and irradiated with visible light. The choice of enzyme is determined by the intended use of the stabilized enzyme system. While not wishing to be bound by theoretical considerations, it is now believed that the "activated matrix", by photolysis, forms an arylnitrene which, in turn, forms stable covalent bonds with enzymes. In any event, binding of a desired enzyme to the "activated matrix" is accomplished by contacting the activated matrix with the desired enzyme and irradiating the mixture with electromagnetic radiation of a wave length falling in the visible spectrum. The rate of binding reaction depends primarily upon the light intensity. Other conditions such as temperature, pH, etc., are not critical insofar as the photolytic reaction is concerned. These conditions are chosen to optimize the catalytic activity of the enzyme used. Generally applicable conditions are temperature of about 0° to 37°C., a pH of 6 to 8, and atmospheric pressure. The maximum light intensity used is limited by the efficiency of removal of heat transferred to the sample by the light source. In order to avoid possible harm to the enzyme from absorbed ultraviolet light, this light can be passed through clear glass and sodium nitrite solution to remove ultraviolet radiation of wave length shorter than 390 nm. Useful reaction times withh a 100 watt focused tungsten halide light source are about 1 to 20 hours.

Because of the high degree of independence of the reactivity of the photochemical group (e.g., nitrophenylazide) from the reaction condition variables (such as temperature and pH) which control the reactivity of the thermochemical groups, this process using a photochemical-thermochemical class of bifunctional reagents to prepare activated support materials, offers numerous important advantages over enzyme immobilization processes and materials heretofore reported. In contrast to most activated support materials now available from supply houses or reported in the scientific literature, such materials activated in the dark by reaction with the proper thermochemical-photochemical derivative will be stable for storage in the dark indefinitely. These purified activated support materials can be used to bind enzymes by a very simple reaction procedure under conditions of pH, temperature and ionic content chosen for optimum stability of the enzyme instead of optimum immobilization rate.

The following numbered examples further illustrate the invention and the advantages thereof.

EXAMPLE 1

About 100 milligrams of white, fine granular, dry alkylamine glass [(AAG), (ENCOR, 550 A, 40–80 mesh, porous glass beads, Corning Biomaterials)] were added to 1 milliliter of about 0.9M sodium borate buffer (pH 9.1) in an amber glass bottle. 1-Fluoro-2-nitro-4-azidobenzene (FNAB), about 16 milligrams, was dissolved in 2 milliliters ethanol in dim light and added to the reaction bottle. This mixture was stirred at 37°C. for 20 hours in the dark. The solid product was separated and washed with ethanol, with 3M sodium chloride, and with 0.02M potassium phosphate buffer, pH 8. The washed solid nitroazidophenyl-aminoalkyl glass product (fine pink granules) was dried under vacuum at room temperature and stored at this temperature. The preceding operations were performed in the dark or dim light.

Still under dim light, about 75 milligrams of this nitroazidophenyl-aminoalkyl glass (NAP-AAG) derivative and about 7 milligrams of L-Asparaginase (AsNase) from *Escherichia coli* B were placed in a colorless glass round-bottom flask of about 5 milliliter capacity. To this was added about 0.5 milliliter water. This mixture was exposed with stirring under refrigeration (0°–15° C.) to light from a focused 40 watt tungsten lamp passing through about 0.5 centimeter of 1M aqueous sodium nitrite solution for about 16 hours. The solid glass-bound enzyme product (AsNasc-ANP-AAG) was washed sequentially with assay buffer (0.2M phosphate, pH 8), 3M sodium chloride, and assay buffer, then dried under vacuum at room temperature. This dry pink glass-asparaginase was found by a standard enzyme assay (in 0.02M phosphate buffer, pH 8, at 37° C., with 15 millimolar L-asparagine) to exhibit 1450 I.U. enzyme activity per gram of product (1 I.U. is defined as the production of 1 micromole product per minute under the assay conditions).

The pink granular powder resulting from the above procedures comprises a stabilized immobilized enzyme system having high catalytic efficiency and specificity, capable of accelerating the amido-hydrolysis of L-asparagine without extremes of pH or temperature. This enzyme system can be used to convert L-asparagine to L-aspartic acid and ammonia under very mild reaction conditions with very low energy requirements and minimal side reactions or undesirable byproducts. This form of the catalyst can be readily recovered for subsequent use in either batch or flow processes for conversion of dissolved L-asparagine or aspartic acid and ammonia. Also, bound to an ammonium ion-sensitive electrode membrane, the glass-bound enzyme can be used to quantitatively measure L-asparagine concentration in physiological and other fluids.

EXAMPLE 2

Activated cellulose derivative (nitroazidophenyl-aminoethyl cellulose (NAP-AEC) was prepared from 1-fluoro-2-nitro-4-azidobenzene and amino ethyl cellulose in the dark with subdued daylight for the beginning and ending operations. About 100 milligrams of aminoethyl cellulose (AEC) (Bio.Rad Cellex-AE, Control No. 10490, 0.37 milliequivalent/gram was suspended in 1 milliliter of about 0.05M sodium bicarbonate buffer (pH 7–7.5) in an amber or opaque container. To this suspension was added 1 milliliter ethanol. 1-Fluoro-2-nitro-4-azidobenzene (9.1milligram) in 0.5 milliliter ethanol was added to the suspension, followed by 0.5 milliliter ethanol wash. The reaction mixture was stoppered and stirred in the dark at room temperature (about 24° C.) for 17 hours. The solid product was separated and washed with ethanol, with 3M sodium chloride, and with 0.02M potassium phosphate buffer, pH 8. The washed solid product was dried under vacuum at room temperature. The dry, fibrous, yellow-pink powder (NAP-AEC) was stored at room temperature in the dark. The preceding operations were performed in the dark or in subdued daylight.

The immobilization of asparaginase on this activated support matrix was accomplished by exposure of the mixture to visible light for about 16 hours at 0°–15° C. About 20 milligrams nitroazidophenyl-aminoethyl cellulose (NAP-AEC) were mixed with 3 milligrams L-Asparaginase in 0.25 milliliter water contained in an approximately 5 milliliter colorless glass round-bottom flask covered at the mouth with a gum rubber dropper bulb. This slurry was stirred magnetically at 0°–15° C. for about 16 hours with illumination from a focused 8 volt, 5 amp microscope illuminator light passing through about 0.5 centimeter of 1M aqueous sodium nitrite in a glass Petri dish. The solid cellulose-bound enzyme product (AsNase-ANP-AEC) was washed sequentially with assay buffer (0.02M phosphate, pH 8), 3M sodium chloride, an assay buffer, then dried under vacuum at room temperature. This washed, dried, slightly pink product (AsNase-ANP-AEC) is a fibrous fluffy powder with stabilized catalytic activity (1200I.U./gm.). It can be used for the hydrolysis of L-asparagine and other substrates.

EXAMPLE 3

The activated support material (NAP-AEC) was prepared from 1-fluoro-2-nitro-4-azidobenzene (FNAB) and aminoethyl cellulose (AEC) reacting in borate buffer (pH 9.1) in the dark with subdued daylight for the beginning and ending operations. About 500 milligrams aminoethyl cellulose (AEC) (Bio Rad Cellex-AE, control No. 10480, 0.37 meg/gm) were suspended in 5 milliliters 0.9M borate buffer, pH 9.1, in an Erlenmeyer flask wrapped with aluminum foil. To this was added about 250 milligrams 1-fluoro-2-nitro-4-azidobenzene (FNAB) in 0.5 milliliter acetone. This reaction mixture was covered and mixed by shaking at 37° C. in the dark for 18 hours. The solid reaction product (NAP-AEC) was washed with ethanol and with water under subdued daylight, then dried under vacuum in the dark at room temperature. This dry, fibrous, yellowpink powder (NAP-AEC) was stored at room temperature in the dark.

Invertase (β-fructofuranosidase from Baker's Yeast-:Sigma) was immobilized on the activated matrix (NAP-AEC) by visible illumination for 5 hours. The activated support material (11.4 milligrams NAP-AEC) was mixed with 3.5 milligrams invertase (Sigma Lot 42C-0210) in water and illuminated at 5–9° C. for 5 hours with a tungsten-halide focused projector lamp (12 volt-100 watt) operated at 10 volts, to obtain the immobilized invertase (Invertase-ANP-AEC) product. The catalytic activity (660 I.U./gm) of this washed material was measured by using 3,5-dinitrosalicylic acid to determine the rate of production of reducing groups from sucrose at pH 4.7, 37° C.

This immobilized invertase catalyzes the hydrolysis of glycosidic bonds involving β-D-fructofuranosidase, e.g. sucrose, to yield fructose plus glucose. This form of the catalyst can be readily recovered for subsequent use in either batch or flow processes for converting sucrose to glucose plus fructose.

EXAMPLE 4

An activated matrix (NAP-AAG) was prepared by reacting 1-fluoro-2-nitro-4-azidobenzene with alkylamine glass in the dark at 40° C. in pH 9.1 buffer for 24 hours. About 1 gram alkylamine glass (AAG) (EN-COR, 550 A, 40–80 mesh, porous glass beads, Corning Biomaterials) was placed under subdued daylight in an amber bottle with 10 milliliters of 1M sodium borate buffer, pH 9.1. 1-Fluoro-2-nitro-4-azidobenzene (FNAB) (160 milligrams) in 20 milliliters ethanol was added. This stoppered reaction mixture was stirred in the dark at 40° C. for 24 hours. The solid reaction product was washed successively under subdued daylight with ethanol, 3M sodium chloride and assay buffer (0.02M phosphate, pH 8), then dried under vacuum at room temperature in the dark. The resulting dry pink granular material (NAP-AAG) was stored at room temperature in the dark.

Invertase was immobilized on the activated glass (NAP-AAG) by visible illumination for 18 hours at 0°–8° C. About 56.3 milligrams nitroazidophenyl-alkylamine glass (NAP-AAG) was mixed with 9.4 milligrams invertase (Sigma Lot 42C-0210) in water and illuminated at 0°–8° C. for 18 hours at 7.5 volts with a 12 volt-100 watt focused projector lamp. The washed pink granular powder (Invertase-ANP-AAG) had an enzyme activity of 290 I.U. per gram.

EXAMPLE 5

An activated matrix (NAP-AAG) was prepared by reacting alkylamine glass with 1-fluoro-2,4-dinitrobenzene (FDNB), followed by reduction, diazotization and azide substitution. The alkylamine glass (500 milligrams) was suspended in 5 milliliters of water. To this was added 25 milligrams sodium bicarbonate, followed by 150 ul 1-fluoro-2,4-dinitrobenzene in 4 milliliters ethanol. This reaction mixture was stirred in the dark at 37° C. for 4 hours. The solid product was washed sequentially with ethanol and water, then dried under vacuum and stored in the dark at room temperature. This bright yellow granular powder is designated dinitrophenyl-aminoalkyl glass (DNP-AAG).

To 27 milligrams of the dinitrophenyl-aminoalkyl glass was added 243 milligrams sodium acid sulfide in 5 milliliters methanol. Stirring was continued at 30° C. overnight (16 hours). The solid product (lighter yellow or light brown) was washed sequentially with water, ethanol, carbon disulfide, and ethanol. The separated solid material (designated aminonitrophenyl-aminoalkyl glass) was suspended in 2 milliliters concentrated hydrochloric acid at 0°–5° C., and 0.2 gram sodium nitrite in 2 milliliters water was added dropwise over a 2 hour period. Still at 0°–5° C., 200 milligrams sodium azide in a minimum volume of water was added dropwise and the mixture allowed to stand for 1 hour. The resulting brown granular solid material was washed with water before use. It was designated nitroazidophenyl-aminoalkyl glass.

Invertase was immobilized on the nitroazidophenylaminoalkyl glass prepared in this manner, by visible illumination for 18 hours at 0°–8° C. About 12 milligrams of this activated support material was mixed with 2.5 milligrams invertase (Sigma Lot 42C-0210) in water and illuminated at 0°–8° C. for 18 hours at 7.5 volts with a 12 volt-100 watt focused projector lamp. The washed immobilized enzyme product was dried under vacuum at room temperature.

The resulting light brown granular powder (Invertase-ANP-AAG) had an enzyme activity of 900 I.U. per gram.

EXAMPLE 6

An activated matrix (NAP-AAG) was prepared by reacting 1-fluoro-2-nitro-4-azidobenzene with alkylamine glass in the dark at 40° C. in pH 9.1 buffer for 24 hours. About 1 gram alkylamine glass (AAG) (EN-COR, 550 A, 40-80 mesh, porous glass beads, Corning Biomaterials) was placed under subdued daylight in an amber bottle with 10 milliliters of 1M sodium borate buffer, pH 9.1. 1-Fluoro-2-nitro-4-azidobenzene (FNAB) (160 milligrams) in 20 milliliters ethanol was added. This stoppered reaction mixture was stirred in the dark at 40° C. for 24 hours. The solid reaction product was washed successively under subdued daylight with ethanol, 3M sodium chloride and assay buffer (0.02M phosphate, pH 8), then dried under vacuum at room temperature in the dark. The resulting dry pink granular material (NAP-AAG) was stored at room temperature in the dark.

Horseradish peroxidase was immobilized on the activated matrix by visible illumination at 0°–1° C. for 5 hours. About 25.4 milligrams of nitroazidophenyl-aminoalkyl glass was mixed with about 0.9 milligram horseradish peroxidase (Worthington Biochemical, HPOFF 2LA) in 0.5 milliliter water and illuminated at 10 volts with a 12 volt-100 watt focused projector lamp for 5 hours at 0°–1° C. The immobilized enzyme was washed successively with water, 3M sodium chloride, and assay buffer (0.01M potassium phosphate, pH 6.0 and stored at 4° C.

Peroxidase catalyzes the oxidation of various electron doner compounds by hydrogen peroxide and/or a few organic peroxides. By the Worthington assay using hydrogen peroxide as oxidizing agent and MC&B practical grade o-dianisidine as hydrogen donor, the immobilized enzyme product (peroxidase-ANP-AAG) exhibited 39.6 I.U. per gram dry weight before drying and 8 I.U. per gram dry weight after drying under vacuum at room temperature. This stabilized catalyst can be used in a sensitive detection unit for hydrogen peroxide or other peroxide substrates and in batch or flow processes for the oxidation of electron donor substrates by peroxide substrates of this enzyme.

EXAMPLE 7

An activated matrix (NAP-AAG) was prepared by reacting 1-fluoro-2-nitro-4-azidobenzene with alkylamine glass in the dark at 40° C. in pH 9.1 buffer for 24 hours. About 1 gram alkylamine glass (AAG) (ENCOR, 550 A, 40–80 mesh, porous glass beads, Corning Biomaterials) was placed under subdued daylight in an amber bottle with 10 milliliters of 1M sodium borate buffer, pH 9.1. 1-Fluoro-2-nitro-4-azidobenzene (FNAB) (160 milligrams) in 20 milliliters ethanol was added. This stoppered reaction mixture was stirred in the dark at 40° C. for 24 hours. The solid reaction product was washed successively under subdued daylight with ethanol, 3M sodium chloride and assay buffer (0.02M phosphate, pH 8), then dried under vacuum at room temperature in the dark. The resulting dry pink granular material (NAP-AAG) was stored at room temperature in the dark.

Glucose oxidase from *Aspergillus niger* (a Reagent Grade clear yellow liquid preparation from Research Division of Miles Laboratories, Inc. (Code No. 31-617, Lot 37)) was immobilized on the activated support material by visible illumination under $N_2$ atmosphere at 0°–1° C. for 6 hours. To 22 milligrams of nitroazidophenyl-alkylamine glass (NAP-AAG) was added 1 milliliter of the purchased enzyme solution. The suspension was stirred magnetically in a nitrogen atmosphere with 6 hour exposure to light from a focused tungsten halide lamp (12 volt, 100 watt) operated at 10 volts.

Glucose oxidase catalyzes the combination of glucose and $O_2$ to yield gluconic acid and hydrogen peroxide. By the Worthington assay using horseradish peroxidase to determine the hydrogen peroxide product, the washed immobilized enzyme product (glucose oxidase-ANP-AAG) exhibited 325 I.U. per gram dry weight before drying and 105 I.U. per dry gram after drying under vacuum at room temperature. The commercial enzyme solution yielded an activity of 750 I.U. per milliliter by this assay. This immobilized catalyst can be used in a sensitive quantitative detection unit for glucose in physiological and other fluids.

The advantages of this invention are apparent from the foregoing. Thus, active enzymes can be immobilized and stabilized on solid support materials in which form the enzymes are particularly convenient for use in various applications. The so-stabilized enzyme systems can be used in batch or flow processes with recovery of the enzyme systems being readily accomplished by decantation, filtration and similar procedures. Similarly, the stabilized enzymes can be conveniently employed in reaction columns and the enzyme activity realized by passing desired reactants or substrates through the reaction column. The thermochemical-photochemical activity agents used in preparing the enzyme systems of this invention are characterized by the independence of the reactivity of their dual functionality. The reaction of these activating agents with a solid support material to form the activated matrix can be effected without adversely affecting the capability of the agent to achieve covalent cross-linking of an enzyme with the matrix. These activated support materials can be stored for an indefinite period of time, then used to bind or immobilize enzymes with very simple and mild reaction conditions which yield immobilized enzymes with high catalytic efficiencies.

Those modifications and equivalents which fall within the spirit of the invention are to be considered a part thereof.

What is claimed is:

1. A process for immobilization of an active enzyme on a solid support material which comprises:
   a. thermochemically attaching to a solid support material an aryl azide bifunctional agent initially possessing both a thermochemically active functional substituent and a photochemically active functional substituent;
   b. photochemically activating the azide substituent of the product of step (a); and
   c. reacting the photoactivated azide substituent of the product of step (b) with an enzyme to form a covalent linkage therewith.

2. The process of claim 1 wherein step (a) is carried out in the absence of visible light of such intensity as to substantially affect the photochemically active functional substituent of the bifunctional agent.

3. A process in accordance with claim 1 wherein the solid support material is selected from the group consisting of alkylamine glass and aminoethyl cellulose.

4. A process in accordance with claim 1 wherein the solid support material is alkylamine glass and the bifunctional agent is 1-fluoro-2-nitro-4-azidobenzene.

5. A process in accordance with claim 1 wherein the solid support material is alkylamine glass and the bifunctional agent is 1-fluoro-2,4-dinitro-5-azidobenzene.

6. A process in accordance with claim 1 wherein the solid support material is aminoethyl cellulose and the bifunctional agent is 1-fluoro-2-nitro-4-azidobenzene.

7. A process in accordance with claim 1 wherein the solid support material is aminoethyl cellulose and the bifunctional agent is 1-fluoro-2,4-dinitro-5-azidobenzene.

8. A process in accordance with claim 1 wherein the solid support material is an agarose.

9. An active enzyme immobilized on a solid support material produced in accordance with the process of claim 1.

10. An active enzyme immobilized on a solid support material produced in accordance with the process of claim 3.

11. An active enzyme immobilized on a solid support material produced in accordance with the process of claim 4.

12. An active enzyme immobilized on a solid support material produced in accordance with the process of claim 5.

13. An active enzyme immobilized on a solid support material produced in accordance with the process of claim 6.

14. An active enzyme immobilized on a solid support material produced in accordance with the process of claim 7.

15. An active immobilized enzyme in accordance with claim 9 wherein the covalently bound enzyme is asparaginase.

16. An active immobilized enzyme in accordance with claim 9 wherein the covalently bound enzyme is invertase.

17. An active immobilized enzyme in accordance with claim 9 wherein the covalently bound enzyme is peroxidase.

18. An active immobilized enzyme in accordance with claim 9 wherein the covalently bound enzyme is glucose oxidase.

19. A process for immobilization of an active enzyme on a solid support material which comprises
   a. reacting alkylamine glass with 1-fluoro-2,4-dinitrobenzene to form a dinitrophenyl derivative of the alkylamine glass;
   b. reducing the dinitrophenyl derivative to form an aminonitrophenyl derivative of alkylamine glass;
   c. treating the aminonitrophenyl derivative of alkylamine glass with nitrous acid to form a nitrophenyldiazonium derivative of alkylamine glass;
   d. substituting the nitrophenyldiazonium derivative with an azide ion to form a nitroazidophenyl derivative of alkylamine glass;
   e. photochemically activating the nitroazidophenyl derivative of alkylamine glass; and
   f. reacting the photochemically activated product of step (e) with an enzyme to form a covalent linkage therewith.

20. An active enzyme immobilized on a solid support material produced in accordance with the process of claim 19.

21. A process for immobilization of an active enzyme on a solid support material which comprises
   a. reacting aminoethyl cellulose with 1-fluoro-2,4-dinitrobenzene to form a dinitrophenyl derivative of the aminoethyl cellulose;
   b. reducing the dinitrophenyl derivative to form an aminonitrophenyl derivative of aminoethyl cellulose;
   c. treating the aminonitrophenyl derivative of aminoethyl cellulose with nitrous acid to form a nitrophenyldiazonium derivative of aminoethyl cellulose;
   d. substituting the nitrophenyldiazonium derivative with an azide ion to form a nitroazidophenyl derivative of aminoethyl cellulose;
   e. photochemically activating the nitroazidophenyl derivative of aminoethyl cellulose; and
   f. reacting the photochemically activated product of step (e) with an enzyme to form a covalent linkage therewith.

22. An active enzyme immobilized on a solid support material produced in accordance with the process of claim 21.

* * * * *

UNITED STATES PATENT OFFICE
CERTIFICATE OF CORRECTION

PATENT NO. : 3,959,078
DATED : May 25, 1976
INVENTOR(S) : Patrick E. Guire

It is certified that error appears in the above-identified patent and that said Letters Patent are hereby corrected as shown below:

Column 2, line 20, after "preferred" delete "visible"

Column 6, line 15, "or" should be -- to -- line 29, after "gram" insert -- ) -- line 63, "(1200I.U./gm)" should be -- (1200 I.U./gm) --

Column 7, line 13, "yellowpink" should be -- yellow-pink --

Column 8, line 25, "phenylaminoalkyl" should be -- phenyl-aminoalkyl -- line 64, "6.0and" should be -- 6.0) and --

Signed and Sealed this

Twenty-eighth Day of September 1976

[SEAL]

Attest:

RUTH C. MASON
*Attesting Officer*

C. MARSHALL DANN
*Commissioner of Patents and Trademarks*